United States Patent [19]
Narita

[11] Patent Number: 5,226,069
[45] Date of Patent: Jul. 6, 1993

[54] X-RAY IMAGING APPARATUS

[75] Inventor: Sukekiyo Narita, Ootawara, Japan

[73] Assignee: Kabushiki Kaisha Toshiba, Kawasaki, Japan

[21] Appl. No.: 799,933

[22] Filed: Nov. 29, 1991

[30] Foreign Application Priority Data

Nov. 30, 1990 [JP] Japan .................. 2-340418

[51] Int. Cl.[5] ............................................. H05G 1/02
[52] U.S. Cl. .................................. 378/197; 378/195; 378/196; 378/189
[58] Field of Search ............... 378/197, 193, 194, 196, 378/195, 198, 189, 167, 177

[56] References Cited

U.S. PATENT DOCUMENTS 4,481,656 11/1984 Janssen et al. .................. 378/196
4,501,011 2/1985 Hauck et al. .................... 378/196

Primary Examiner—David P. Porta
Assistant Examiner—Don Wong
Attorney, Agent, or Firm—Oblon, Spivak, McClelland, Maier & Neustadt

[57] ABSTRACT

An X-ray imaging apparatus comprises a base installed in an examination room, an intermediate frame coupled to the base via a horizontal first rotary shaft, an arm coupled to the intermediate frame via a horizontal second rotary shaft, a mechanism, provided at one end portion of the arm, for removably supporting at least one X-ray generating unit, the X-ray generating unit supported by this mechanism, a mechanism, provided at the other end portion of the arm, for supporting at least one X-ray detection unit, and the X-ray detection unit supported by this mechanism.

21 Claims, 12 Drawing Sheets

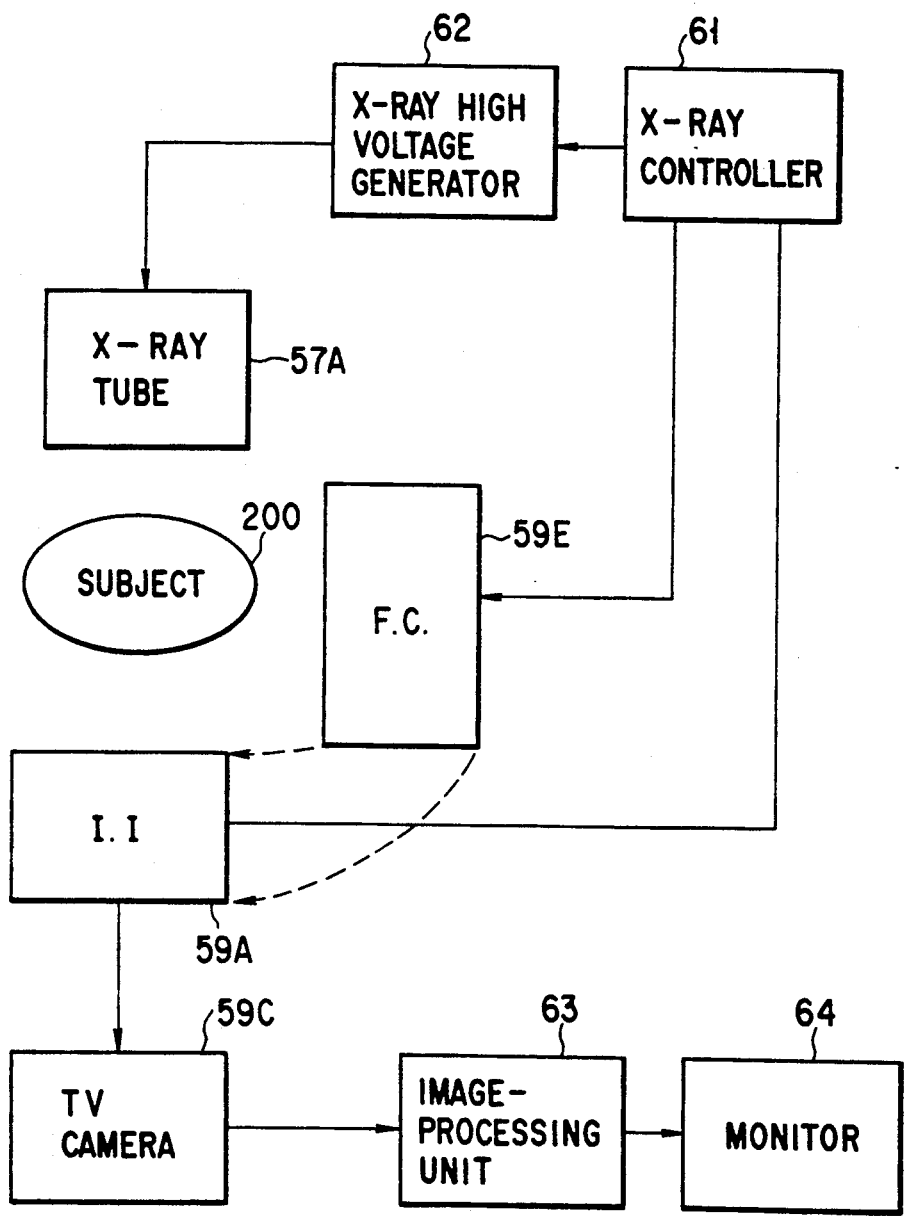
F I G. 12

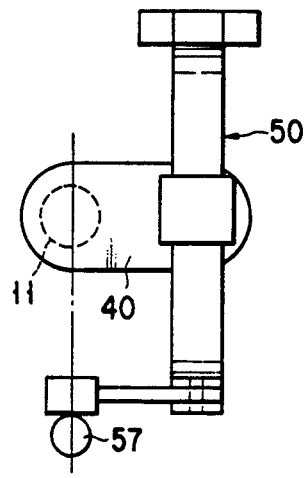
F I G. 15A
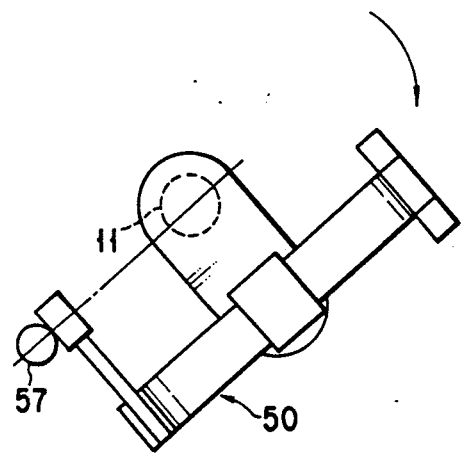
F I G. 15B
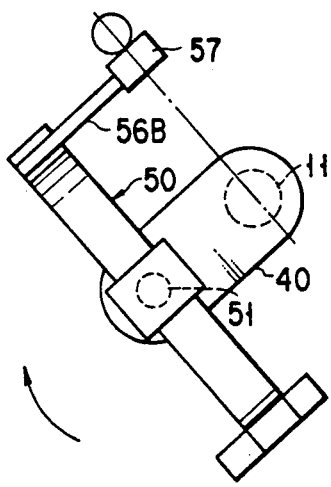
F I G. 15C
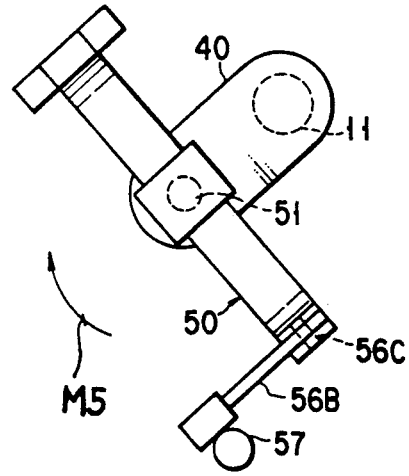
F I G. 15D
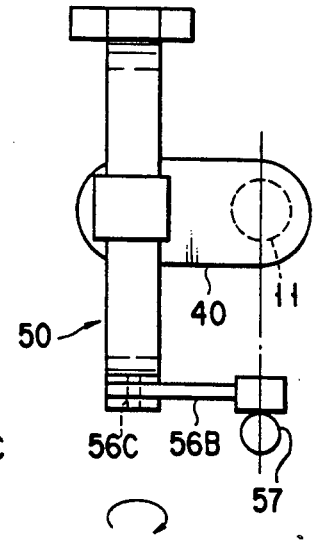
F I G. 15E

X-RAY IMAGING APPARATUS

BACKGROUND OF THE INVENTION

1. Field of the Invention

The present invention relates to an X-ray imaging apparatus suitable for X-ray diagnosis of circulatory organs.

2. Description of the Related Art

A conventional X-ray imaging apparatus for circulatory organs will now be described with reference to FIG. 1. FIG. 1 shows schematically a ceiling type circulatory organ diagnosis X-ray imaging apparatus. As shown in FIG. 1, a base 1 is mounted on a ceiling 100. The base 1 is connected to a c-arm apparatus via an intermediate arm 2. Base 1 is extendible in the direction of a double headed arrow M1. The intermediate arm 2 has a horizontal rotary shaft 2A and is rotatable in the direction of a double-headed arrow M2 in respect of the base 1. The c-arm apparatus 3 has an arm base 3A which is extendible in a horizontal direction, and also has a c-arm 3B which is slidable in the direction of a double-headed arrow M3 via the arm base 3A. One end portion of the c-arm 3B is provided with an X-ray generating unit 3C such as an X-ray tube and a diaphragm device, and the other end portion thereof is provided with an X-ray detection unit 3D such as an image intensifier ("I.I."), an optical system, a TV camera, a film changer fixing member, and a film changer ("F.C.").

A subject 200 placed on a bed (not shown) is situated between the X-ray generating unit 3C and the X-ray detection unit 3D of the c-arm 3B. Thus, those faces of the subject 200, which look to the X-ray generating unit 3C and the X-ray detection unit 3D can be fluoroscopically diagnosed or photographed.

The c-arm 3B having the X-ray generating unit 3C and X-ray detection unit 3D is situated on the left of the subject 200. This arrangement is generally called "left-offset arrangement."

When the above-described X-ray imaging apparatus is employed, there is a case where a doctor stands on one side of the subject 200 or the top plate, and the doctor performs diagnosis or medical treatment on the subject 200. In such a case, the c-arm apparatus 3 may prevent the doctor from diagnosing the subject, when a certain part of the subject is to be diagnosed for a specific purpose.

When the subject 200 is to be accessed from the right, a left-offset arrangement is suitable; when the subject 200 is to be accessed from the left, a right-offset arrangement is suitable. In particular, the right-offset arrangement is desirable when a catheter is inserted into the left arm of the subject 200.

With the above-described conventional apparatus, however, only the left-offset arrangement is allowed, and the apparatus fails to meet demands for various diagnoses.

On the other hand, this type of X-ray imaging apparatus must be provided with suitable X-ray generating unit 3C or X-ray detection unit 3D, depending on parts to be diagnosed. For example, when the heart is to be diagnosed, a small-diameter (e.g. 9 inches) I.I., if employed as X-ray detection unit 3D, is advantageous in clinical angling, etc.; however, when the legs are to be diagnosed, a large-diameter (e.g. 16 inches) I.I. and F.C. need to be employed for maintaining a wide photographing area.

In the conventional apparatus, however, the c-arm apparatus 3 is provided with only one kind of X-ray generating unit 3C and X-ray detection unit 3D, and demands for various diagnoses are not met.

SUMMARY OF THE INVENTION

The object of the present invention is to provide an X-ray imaging apparatus capable of meeting demands for various diagnoses.

This object can be achieved by an X-ray imaging apparatus comprising:

a base installed in an examination room;

an intermediate frame coupled to the base via a horizontal first rotary shaft; and an arm apparatus coupled to the intermediate frame via a horizontal second rotary shaft, and having X-ray generating means and X-ray detection means.

The above object can also be achieved by an X-ray imaging apparatus comprising:

a base installed in an examination room;

an intermediate frame coupled to the base via a horizontal first rotary shaft;

an arm coupled to the intermediate frame via a horizontal second rotary shaft;

a first mechanism, provided at one end portion of the arm, for removably supporting at least one X-ray generating means;

the X-ray generating means supported by the first mechanism;

a second mechanism, provided at the other end portion of the arm, for supporting at least one X-ray detection means; and the X-ray detection means supported by the second mechanism.

The above object can also be achieved by an X-ray imaging apparatus comprising:

a base installed in an examination room;

an intermediate frame coupled to the base via a horizontal first rotary shaft;

an arm coupled to the intermediate frame via a horizontal second rotary shaft;

a first member, provided at one end portion of the arm, for setting at least one X-ray generating means in a predetermined position in a direction perpendicular to the direction in which the arm extends;

the X-ray generating means supported by the first member;

a second member, provided at the other end portion of the arm, for setting at least one X-ray detection means in a predetermined position in a direction perpendicular to the direction in which the arm extends; and the X-ray detection means supported by the second member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 3A to 3C show in detail the structures of the circulatory organ diagnosing X-ray imaging apparatus according the embodiment of the invention, wherein FIG. 3A is a top view, FIG. 3B is a front view and FIG. 3C is a side view;

FIGS. 5A to 5C show a groove mechanism of a coupling mechanism for the X-ray detection unit according to the embodiment, wherein FIG. 5A is a top view, FIG. 5B is a front view and FIG. 5C is a side view;

FIGS. 6A to 6C show a key mechanism of the coupling mechanism for the X-ray detection unit according to the embodiment, wherein FIG. 6A is a top view, FIG. 6B is a front view and FIG. 6C is a side view;

FIGS. 7A to 7C show the large-diameter I.I. according to the embodiment, wherein FIG. 7A is a top view, FIG. 7B is a front view and FIG. 7C is a side view;

FIGS. 8A to 8C show the small-diameter I.I. according to the embodiment, wherein FIG. 8A is a top view, FIG. 8B is a front view and FIG. 8C is a side view;

FIGS. 9A to 9C show the film changer according to the embodiment, wherein FIG. 9A is a top view, FIG. 9B is a front view and FIG. 9C is a side view;

FIG. 12 is an electrical circuit diagram for X-ray radiation and X-ray image detection according to the embodiment;

FIGS. 14A to 14C show the states in which imaging is carried out with the left-offset arrangement, wherein FIG. 14A is a top view, FIG. 14B is a front view and FIG. 14C is a side view;

FIGS. 15A to 15E illustrate the operation of the embodiment, wherein FIG. 15A is a side view showing the state in which imaging is carried out with the left-offset arrangement, FIG. 15B is a side view showing the intermediate arm rotated clockwise about 90° from the state of FIG. 15A, FIG. 15C is a side view showing the intermediate arm rotated clockwise about 270° from the state of FIG. 15A, FIG. 15D is a side view showing the arm apparatus rotated clockwise about 180° from the state of FIG. 15C, and FIG. 15E shows the support rod inverted from the state of FIG. 15D for carrying out imaging with the right-offset arrangement;

FIGS. 16A to 16C show the state in which imaging is carried out with the right-offset arrangement shown in FIG. 15E, wherein FIG. 16A is a top view, FIG. 16B is a front view and FIG. 16C is a side view; and FIGS. 17A to 17D illustrate the operation of the other embodiment, wherein FIG. 17A shows the state in which imaging with the left-offset arrangement is carried out by using the small-diameter I.I., FIG. 17B shows the state in which imaging with the right-offset arrangement is carried out by using the small-diameter I.I., FIG. 17C shows the state in which imaging with the right-offset arrangement is carried out by using the large-diameter I.I., and FIG. 17D shows the state in which imaging with the left-offset arrangement is carried out by using the large-diameter I.I.

DETAILED DESCRIPTION OF THE PREFERRED EMBODIMENTS

Figure 1:
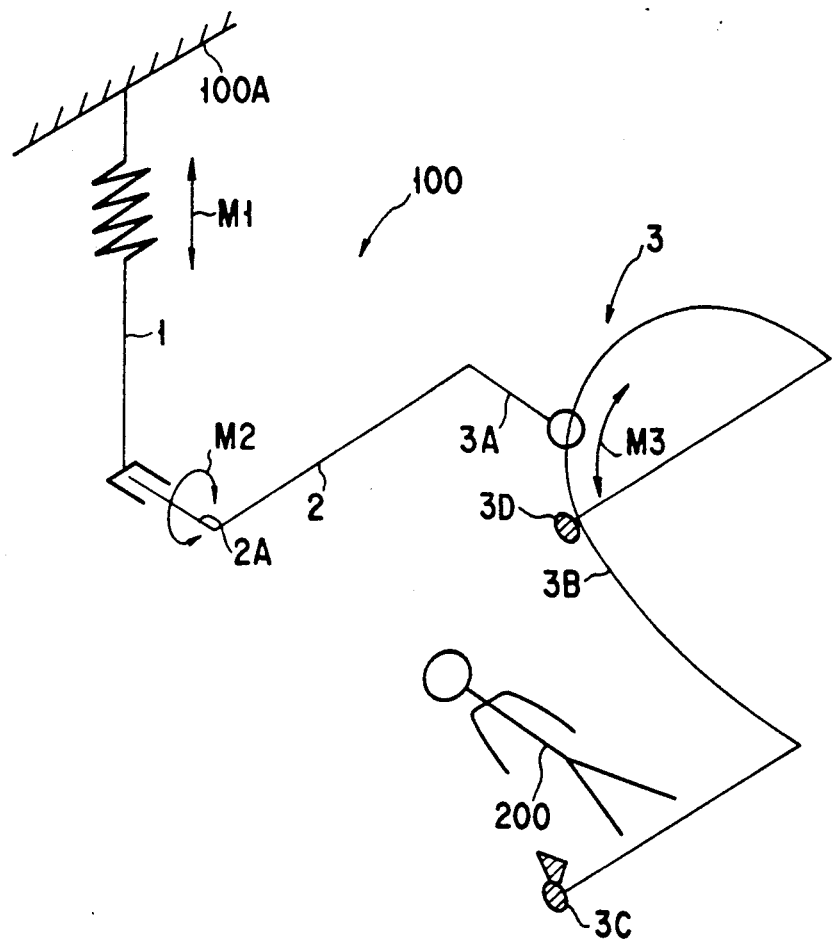
FIG. 1 is a perspective view schematically showing a conventional circulatory organ diagnosing X-ray imaging apparatus.
Figure 2:
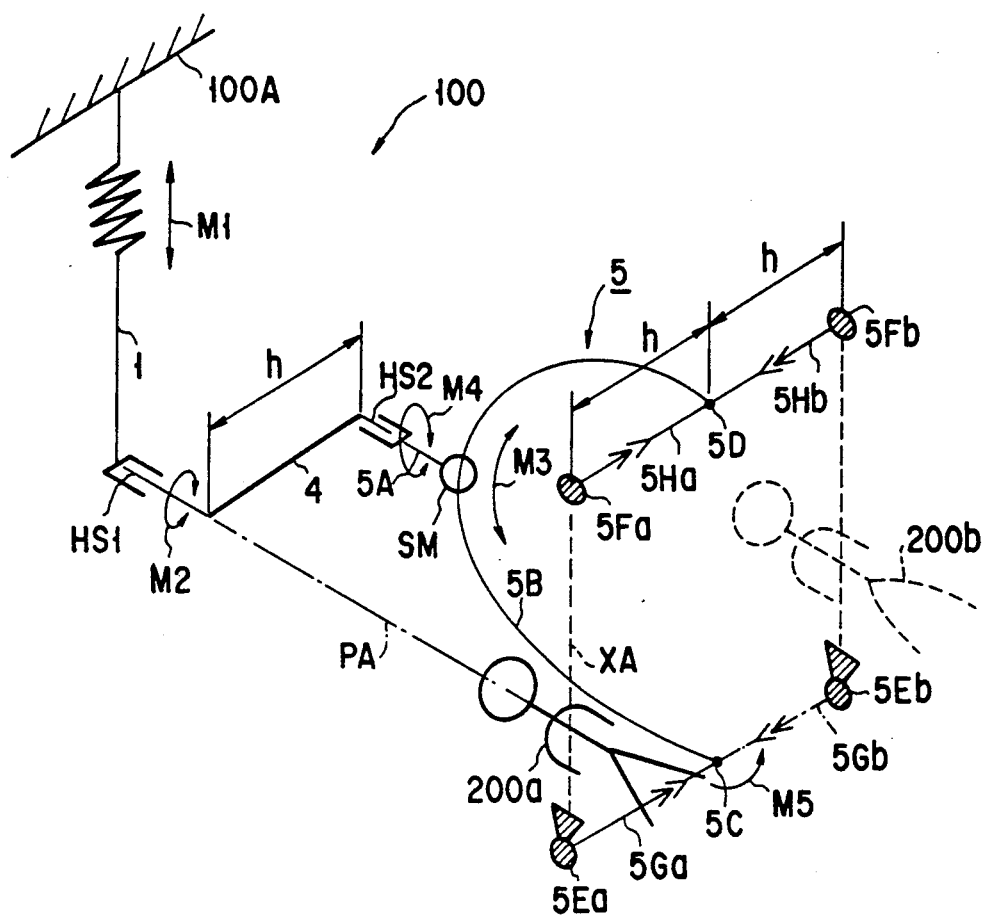
FIG. 2 is a perspective view schematically showing a circulatory organ diagnosing X-ray imaging apparatus according to an embodiment of the present invention.

FIG. 2 shows schematically a ceiling type circulatory organ X-ray imaging apparatus according to an embodiment of the present invention. As shown in FIG. 2, a base 1 is mounted in an examination room 100. For example, the base 1 is mounted on the ceiling 100A of the room 100. The base 1 is coupled to a c-arm apparatus 5 via an intermediate frame 4. The base 1 is extendible in the direction of a double-headed arrow M1. The base 1 can be mounted on the floor or wall of the room 100, as well as the ceiling 100A.

The intermediate frame 4 has a horizontal rotary shaft HS1 which is rotatable in the direction of a double-headed arrow M2 in respect of the base 1. In addition, the c-arm apparatus 5 has a horizontal rotary shaft HS2 which is rotatable in the direction of a double-headed arrow M4 in respect of the intermediate frame 4.

The horizontal rotary shaft HS1 for rotating the intermediate frame 4 and the horizontal rotary shaft HS2 for rotating the c-arm apparatus 5 are distanced between one and the other end portions of the intermediate frame 4 along the longitudinal axis of the frame 4.

An imaginary line PA which extends from the base-side horizontal rotary shaft HS1 of the intermediate frame 4 intersects a line XA obtained by connecting an X-ray generating unit 5E (5Ea, 5Eb) and an X-ray detection unit 5F (5Fa, 5Fb). This is a very important feature in the present embodiment.

It is also important that the intermediate frame 4 has horizontal rotary shafts at one and the other end portions thereof along the longitudinal axis.

The distance between the horizontal rotary shaft HS1 and the horizontal rotary shaft HS2 is "h". When the arm apparatus 5 is vertically situated, as shown in FIG. 2, the distance "h" coincides with the distance between a coupling mechanism 5C and the X-ray generating unit 5Ea, the distance between the coupling mechanism 5C and the X-ray generating unit 5Eb, the distance between a coupling mechanism 5D and the X-ray generating unit 5Fa, and the distance between the coupling mechanism 5D and the X-ray generating unit 5Fb. In other words, arms 5Ga, 5Gb, 5Ha and 5Hb of the c-arm apparatus 5 have the same length, which is also important in this embodiment.

On the other hand, the c-arm apparatus has an arm base 5A which is horizontally extendible in respect of the intermediate frame 4. One end portion of the arm base 5A is provided with a slide mechanism SM. A c-arm 5B is slidable in the direction of a double-headed arrow M3 via the slide mechanism SM.

One end portion of the c-arm 5B is provided with X-ray generating units 5E such as an X-ray tube and a diaphragm device via the coupling mechanism 5C, such that the units 5E are rotatable about the one end portion. The other end portion of the c-arm 5B is provided with X-ray detection units 5Fa and 5Fb such as an I.I., an optical system, a TV camera, an F.C. fixing member and an F.C. via the other coupling mechanism 5D. The X-ray generating unit 5Ea is coupled to the coupling mechanism 5C by means of the arm 5Ga, the X-ray generating unit 5Eb is coupled to the coupling mechanism 5C by means of the arm 5Gb, the X-ray detection unit 5Fa is coupled to the coupling mechanism 5D by means of the arm 5Ha, and the X-ray detection unit 5Fb is coupled to the coupling mechanism 5D by means of the arm 5Hb.

A subject 200 (200a, 200b) is placed on a bed (not shown) between the X-ray generating unit 5E and the X-ray detection unit 5F of the c-arm 5B. Thus, those faces of the subject 200, which look to the X-ray generating unit 5E and X-ray detection unit 5F, can be fluoroscopically diagnosed or photographed.

The c-arm 5B having the X-ray generating unit 5Ea and X-ray detection unit 5Fa is situated on the left of the subject 200a. This arrangement is generally called "left-offset arrangement." The X-ray generating units 5E are rotated (in the direction of M5) by the coupling mechanism 5C about the coupling point therebetween, thereby setting the units 5E at the position indicated by broken lines. Thus, the c-arm 5B having the shifted X-ray generating unit 5Eb and the X-ray detection unit 5Fb is situated in the right-offset arrangement for the subject 200b.

Specific examples of the X-ray imaging apparatus according to the present embodiment shown schematically in FIG. 2 will now be described in detail with reference to FIGS. 3A, 3B and 3C through FIG. 13.

Figure 3A:
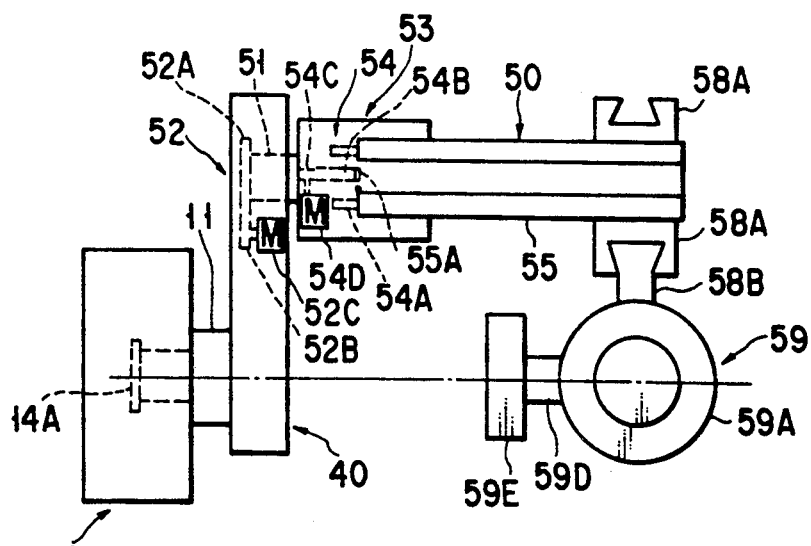
Figure 3B:
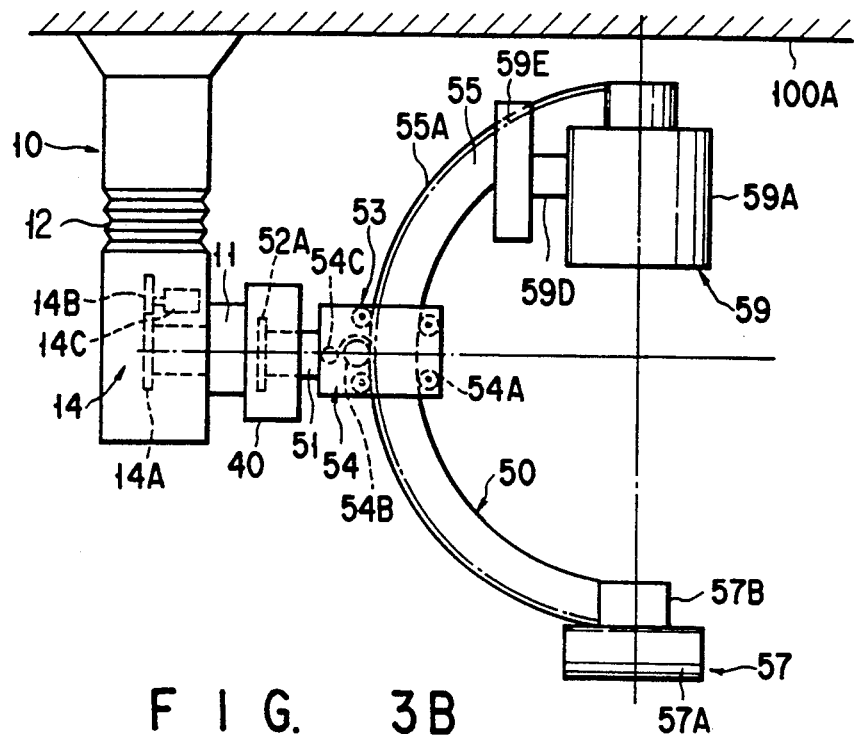
Figure 3C:
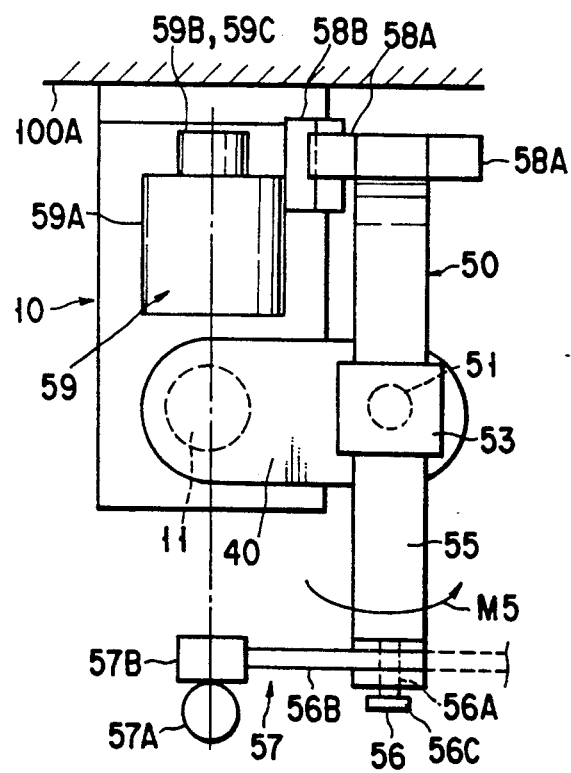

A base 10 (corresponding to base 1 in FIG. 2) is mounted in an examination room 100. As shown in FIGS. 3A, 3B and 3C, the base is mounted on, for example, the ceiling 100A of the room 100. The base 10 is connected to a c-arm apparatus 50 (corresponding to c-arm apparatus 5 in FIG. 2) via an intermediate frame 40 (corresponding to intermediate frame 4 in FIG. 2).

The base 10 is vertically extendible, i.e. in the direction of a double-headed arrow M1. Specifically, one end portion of the base 10 is fixed on the ceiling 100A, and a horizontal rotary shaft 11 (corresponding to horizontal rotary shaft HS1 in FIG. 2) extends from the other end portion of the base 10. Although this base 10 is of the fixed type, a movable base may be employed. The movable base is widely used in this type of circulatory organ diagnosing systems, and the movable base runs on rails provided on the ceiling or floor. Thus, the example shown in the figures should be considered as a typical one.

Figure 4:
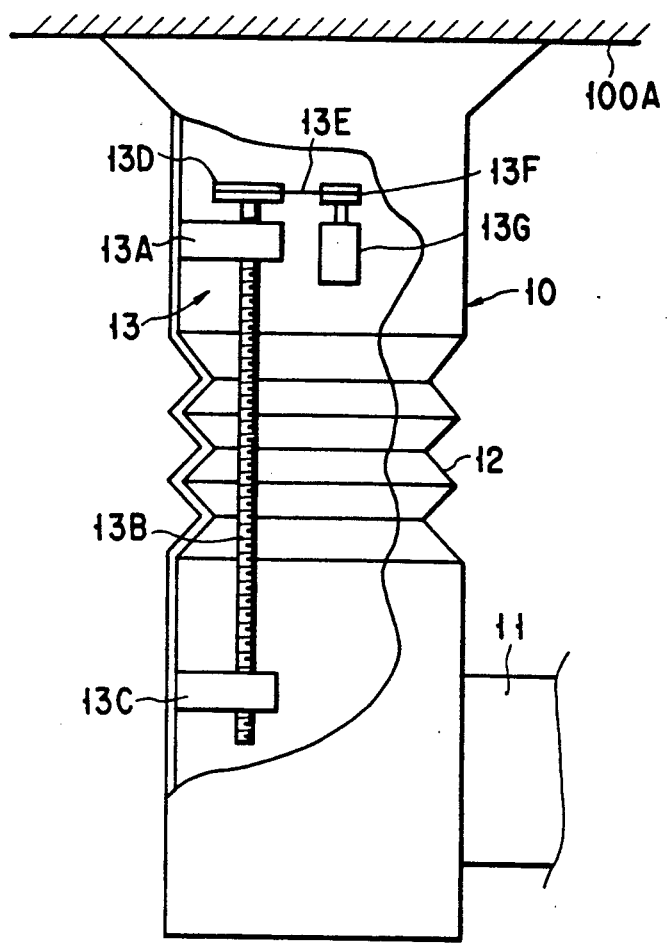
FIG. 4 shows in detail the base in the embodiment, with a portion thereof exploded.
Figure 5A:
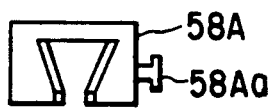
Figures 5B, 5C:
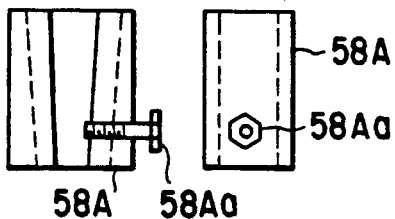
Figure 6A:
Figures 6B, 6C:
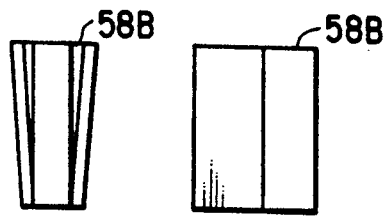

On the other hand, as is shown in FIGS. 3B and 4, a middle portion of the base 10, which is situated along the longitudinal direction of the base 10, is provided with bellows 12 extendible in the direction of M1. The mechanism for extending the bellows 12 is constituted by a lead screw mechanism 13. As is shown in FIG. 4, the lead screw mechanism 13 comprises a fixed bearing 13A fixed on the base 10, a lead 13B screwed in the bearing 13A, a movable bearing 13C fixed on the base 10 and coupled to one axial end portion of the lead 13B, a sprocket 13D provided on the other axial end portion of the lead 13B, a chain 13E passed over the sprocket 13D, another sprocket 13F over which the chain 13E is passed, and a motor 13G including an encoder (not shown) with a rotary shaft fixed to the sprocket 13F.

According to the lead screw mechanism 13, the motor 13G including the encoder (not shown) is rotated suitably, so that the base 10 can desirably be extended, that is, the vertical position of the horizontal rotary shaft 11 can be determined.

As is shown in FIG. 3B, one end portion of the horizontal rotary shaft 11 in the base 10 is provided with an intermediate frame rotating mechanism 14. The mechanism 14 comprises a gear 14A provided at one end of the horizontal rotary shaft 11 in the base 10, another gear 14B meshed with the gear 14A, and a motor 14C including an encoder (not shown) with a rotary shaft coupled to the gear 14B thereby to rotate the gear 14B. The other end portion of the horizontal rotary shaft 11 is coupled to an axial one end portion of the intermediate frame 40 at right angles. According to the intermediate frame rotating mechanism 14, the motor 14C including the encoder (not shown) is suitably rotated to desirably rotate the intermediate frame 40 in respect of the base 10 in the direction of M2. In other words, the rotational position of the intermediate frame 40 in respect of the base 10 can desirably be determined. The rotation in the direction of M2 is the rotation of the intermediate frame 40 in a vertical plane 40.

As is shown in FIG. 3A, a horizontal rotary shaft 51 (corresponding to horizontal rotary shaft HS2 in FIG. 2) of the c-arm apparatus 50 extends from that end portion of the intermediate frame 40, which is opposite to the shaft (11)-side end portion of the frame 40. An end portion of the horizontal rotary shaft 51 in the intermediate frame 40 is provided with an arm base rotating mechanism 52. The mechanism 52 comprises a gear 52A provided at one end of the shaft 51 in the frame 40, another gear 52B meshed with the gear 52A, and a motor 52C including an encoder (not shown) with a rotary shaft connected to the gear 52B thereby to rotate the gear 52B. The other end of the horizontal rotary shaft 51 is connected to the arm base 53 (corresponding to the arm base 5A in FIG. 2).

According to this arm base rotating mechanism 52, the motor 52C including the encoder (not shown) is suitably rotated thereby to desirably rotate the arm base 53 in respect of the intermediate frame 40 in the direction of M4. In other words, the rotational position of the arm base 53 in respect of the intermediate frame 40 can desirably be determined. The rotation in the direction of M3 is the rotation of the c-arm apparatus 50 in a vertical plane.

As is clear from the above, the horizontal rotary shaft 11 for rotating the intermediate frame 40 and the horizontal rotary shaft 51 for rotating the c-arm apparatus (arm base 53) are distanced between one and the other axial end portions of the intermediate frame 40. In addition, the distance between the horizontal rotary shaft 11 and the horizontal rotary shaft 51 is substantially equal to the distance between the center of the c-arm 55 and the X-ray generating unit 57 or X-ray detection unit 59. The axis of the body of the subject is aligned with the axis of the horizontal rotary shaft 11. In fact, the axis of movement of the top plate of the bed is aligned with the axis of the horizontal rotary shaft 11. The axis of the horizontal rotary shaft 11 intersects the line connecting the X-ray generating unit 57 and the X-ray detection unit 59.

In addition, that end portion of the arm base 53 of the c-arm apparatus 50, which is opposite to the frame (40)-side end portion of the arm base 53, is provided with a slide mechanism 54 (corresponding to the slide mechanism SM in FIG. 2). The c-arm 55 (corresponding to the c-arm 5B in FIG. 2) is slidable in the direction of M3 via the slide mechanism 54.

The slide mechanism 54 functions to slide the c-arm 55 of the c-arm apparatus 50 in the direction of M3. A rack gear 55A is formed on the c-arm 55 along its longitudinal axis. The slide mechanism 54 is provided at mutually opposed four corners. The slide mechanism 54 comprises a guide roller 54A for supporting and guiding the c-arm 55, a pinion gear 54B meshed with the rack gear 55A of the c-arm 55, an intermediate gear 54C meshed with the pinion gar 54B, and a motor 54D including an encoder (not shown) with a rotary shaft fixed to the intermediate gear 54C.

According to this slide mechanism, the motor 54D including the encoder (not shown) is suitably rotated thereby to desirably slide the c-arm 55 in respect of the arm base 53 in the direction of M3. That is, a pair of an X-ray generating unit 57 and an X-ray detection unit 59 (described later) can be desirably positioned in relation to the subject (not shown) placed within the c-arm 55.

One end portion of the c-arm 55 is provided with an X-ray generating unit 57 (corresponding to X-ray generating unit 5E in FIG. 2) comprising an X-ray tube, a diaphragm device, etc. via a coupling mechanism 56 (corresponding to coupling mechanism 5C in FIG. 2). The other end portion of the c-arm 55 is provided with an X-ray detection unit 59 (corresponding to X-ray detection units 5Fa, 5Fb) comprising an I.I., an optical system, a TV camera, an F.C. fixing member, an F.C., etc. via another coupling mechanism 58 (corresponding to coupling mechanism 5D in FIG. 2).

The coupling mechanism 56, X-ray generating unit 57, coupling mechanism 58 and X-ray detection unit 59 will now be described in greater detail. Although X-ray generating units 57 can be provided on both sides of the c-arm 55, the coupling mechanism 56 for the X-ray generating unit 57 is constructed, in this embodiment, such that the X-ray generating unit 57 is provided only on one side of the c-arm 55. As is shown in FIGS. 3B and 3C, the coupling mechanism 56 comprises a support member 56A provided at an end portion of the c-arm 55, a support rod 56B (corresponding to arms 5Ga in FIG. 2) supported by the support member 56A so as to be rotatable to the position indicated by broken lines as in the embodiment of FIG. 2, and a support pin 56C for supporting the end portion of the support rod 56B in the support member 56A. The support rod 56B is provided with the X-ray generating unit 57. The X-ray generating unit 57 comprises an X-ray tube 57A and a diaphragm device 57B.

On the other hand, the coupling mechanisms 58 for the X-ray detection unit 59 are provided on both sides of the c-arm 55. The basic structure of the coupling mechanism 58 is a V-key mechanism. Specifically, the coupling mechanism 58 comprises a groove mechanism 58A (shown in FIGS. 3A, 5A, 5B and 5C) and a key mechanism 58B (shown in FIGS. 3A, 6A, 6B and 6C). The groove mechanisms 58A are provided on both sides of the c-arm 55, and the key mechanisms 58B are engaged in the grooves 58A.

The key mechanism 58B is provided with the X-ray detection unit 59. In FIGS. 3A, 3B and 3C, the groove mechanisms 58A are provided on both sides of the c-arm 55, but only one of them is provided with the key mechanism 58B and the X-ray detection unit 59. The groove mechanism 58A is provided with a female screw 58Aa for fixing the X-ray detection unit 59. The X-ray detection unit 59 comprises an I.I. 59A, an optical system 59B, a TV camera 59C, an F.C. fixing member and an F.C. 59E.

According to the above structure, the subject placed on the top plate of the bed (not shown) is situated between the X-ray generating unit 57 and X-ray detection unit 59 of the c-arm 55. Thus, those faces of the subject, which look to the X-ray generating unit 57 and X-ray detection unit 59, can be fluoroscopically diagnosed or photographed.

The c-arm 50 which has the X-ray generating unit 57 and the X-ray detection unit 59, can be situated on the right or left of the subject. That is, the left-offset arrangement or right-offset arrangement can freely be selected. This will be described later by referring to FIGS. 14A to 14C, 15A to 15E, 16A to 16C and 17A to 17D.

The X-ray tube 57A of the X-ray generating unit 57 and the I.I. 59A of the X-ray detection unit 59, which are situated with the left-offset arrangement or right-offset arrangement in respect of the subject 200, can be positioned to interpose the subject 200 and face to each other. In addition, in the X-ray detection unit 59, in place of the I.I. 59A, the F.C. 59E can be rotated by operating the fixing member 59D manually or, if necessary, by means of a motor, so that the F.C. 59E faces the X-ray tube 57A. Thus, fluoroscopic diagnosis or photographing can be effected easily.

Figure 7A:
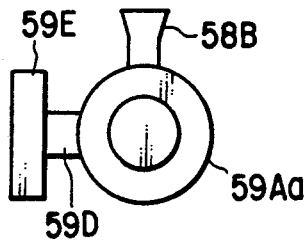
Figure 7B:
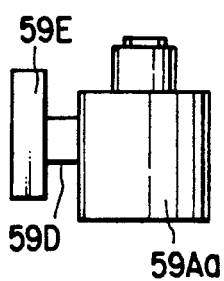
Figure 7C:
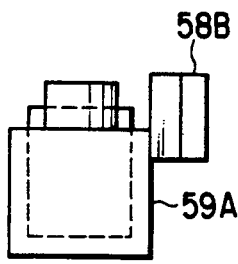
Figure 9A:
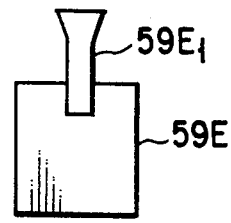
Figure 8A:
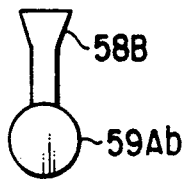
Figure 9B:
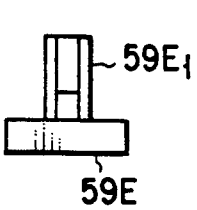
Figure 9C:
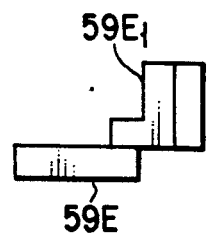
Figure 8B:
Figure 8C:
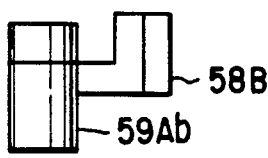

The large-diameter I.I. 59Aa, small-diameter I.I. 59Ab and F.C. 59E of the X-ray detection unit 59 coupled to the coupling mechanism 58 are, respectively, shown in FIGS. 7A, 7B and 7C, FIGS. 8A, 8B and 8C, and FIGS. 9A, 9B and 9C. Specifically, the large-diameter I.I. 59Aa shown in FIGS. 7A, 7B and 7C is provided with F.C. 59E via fixing member 59D. The small-diameter I.I. 59Ab shown in FIGS. 8A, 8B and 8C is provided with coupling mechanism 58B. The F.C. 59E shown in FIGS. 9A, 9B and 9C is solely coupled to the coupling mechanism 58 and has a fixing member 59E1.

Figure 10:
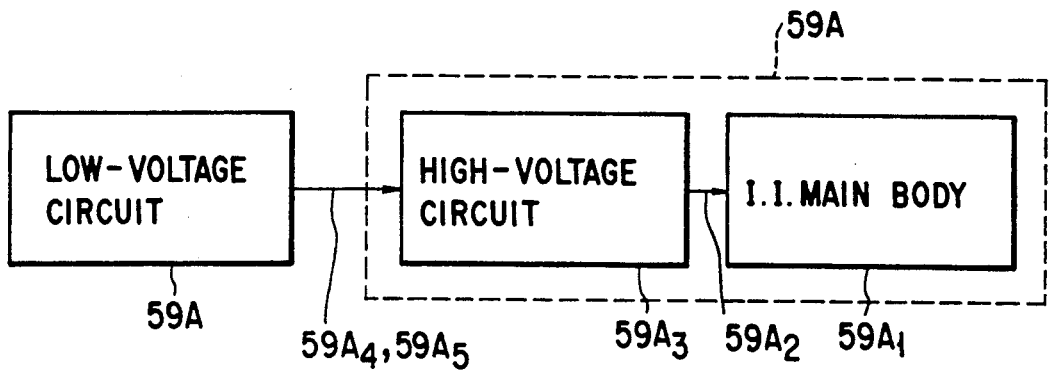
FIG. 10 is a circuit diagram showing an electrical structure of the I.I. in the embodiment.
Figure 11:
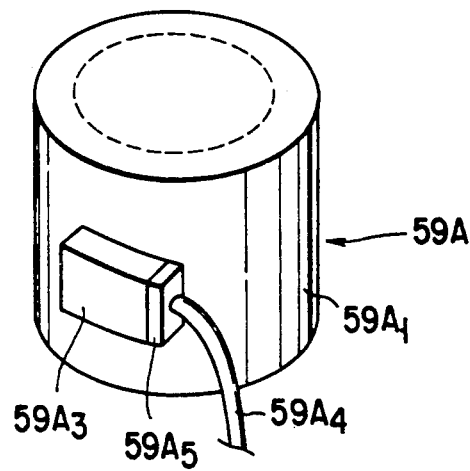
FIG. 11 is a perspective view showing the external appearance of the I.I. in the embodiment.

The I.I. 59 (large-diameter I.I. 59Aa or small-diameter I.I. 59Ab) may have structures shown in FIGS. 10 and 11. As is shown in FIG. 10, the I.I. 59 comprises an I.I. main body 59A1, a high-voltage line 59A2 connected to the body 59A1, and a high-voltage circuit 59A3 connected to the high-voltage line 59A2. The I.I. 59 is connected to a low-voltage circuit 59A via a connector 59A5 and a low-voltage line 59A4.

This structure can easily be understood from FIG. 11. Specifically, the high-voltage circuit 59A3 is attached to the body 59A1. The high-voltage circuit 59A3 is provided with the connector 59A5 so that the low-voltage line 59A4 can freely be connected/disconnected to the high-voltage circuit 59A3. By virtue of this structure, when the I.I. 59 is exchanged, it is not necessary to handle a high-voltage line, unlike the prior art. Only the low-voltage line 59A4 is handled. Further, by detaching the connector 59A5 and exchanging the integrated unit of the main body 59A1 and 59A3, the small-diameter I.I. or large-diameter I.I. can be selected.

An electric circuit for X-ray radiation in the above-described apparatus of the embodiment and the structure of an electric circuit for detection signal processing will now be described with reference to FIG. 12. Specifically, the X-ray tube 57a of the X-ray generating unit 57 is operated by an X-ray controller 61 and an X-ray high voltage generator 62.

The X-ray high voltage generator 72 is controlled by a command from the X-ray controller 61. The detection outputs from the I.I. 59A and TV camera 59C of the X-ray detection unit 59 are supplied to an image-processing unit 63 and the output from the unit 63 is displayed on a monitor 64. The X-ray controller 61 controls not only the X-ray high voltage generator 62, but also the I.I. 59A and F.C. 59E.

Figure 13:
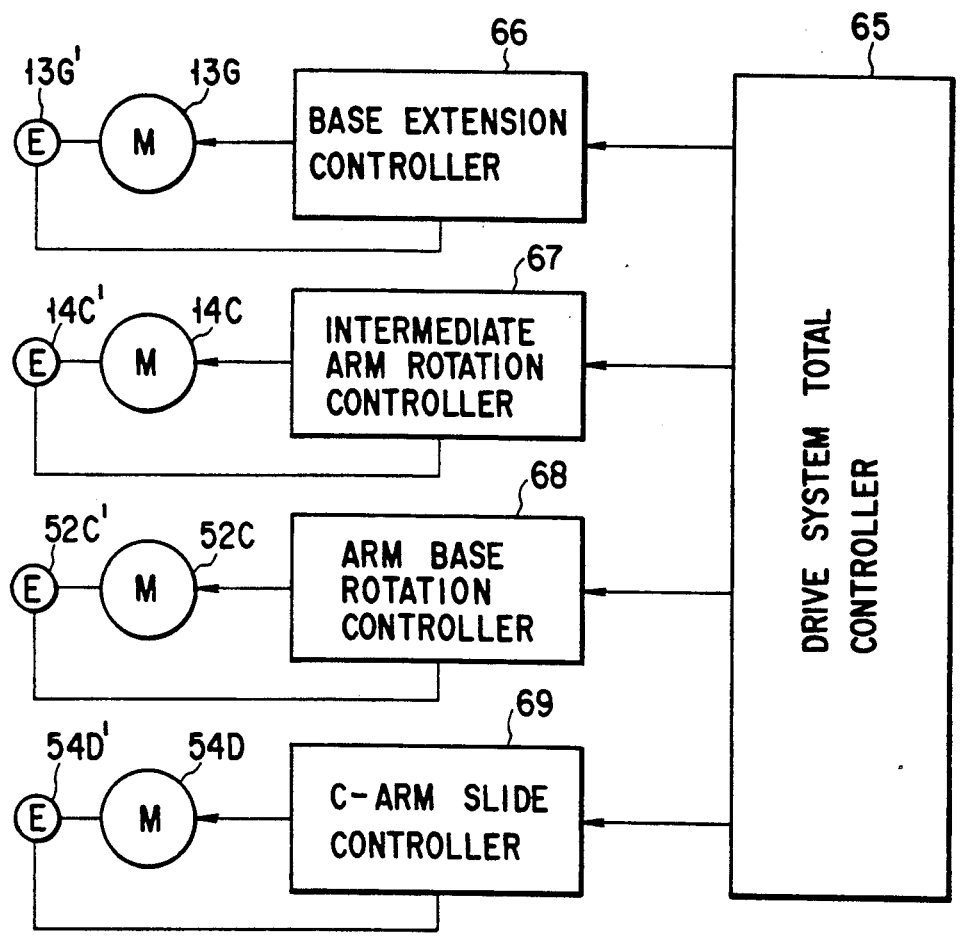
FIG. 13 is an electrical circuit diagram for mechanical drive according to the embodiment.

By referring to FIG. 13, the structure of an electric circuit for mechanically driving the apparatus of the embodiment is shown. The motor 13G for the lead screw mechanism 13 for extension of the base and encoder 13G' is controlled by a base extension controller 66. The motor 14C for the rotating mechanism 14 for rotating the intermediate frame and encoder 14C' are controlled by an intermediate arm rotation controller 67. The motor 52C for the rotating mechanism 52 for rotating the arm base and encoder 52C' are controlled by an arm base rotation controller 68. The motor 54D for the slide mechanism 54 for sliding the c-arm and encoder 54D' are controlled by a c-arm slide controller 69. The controllers 66, 67, 68 and 69 are controlled by a drive system total controller 65.

Figure 14A:
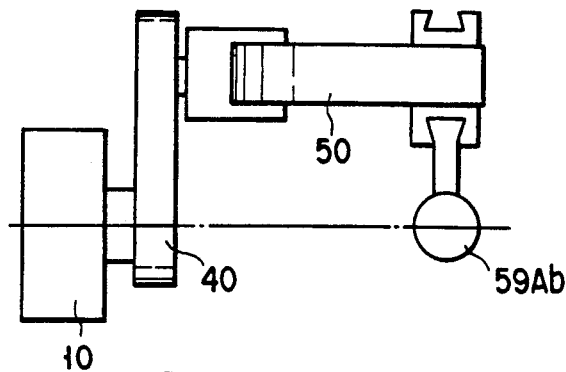
Figure 14B:
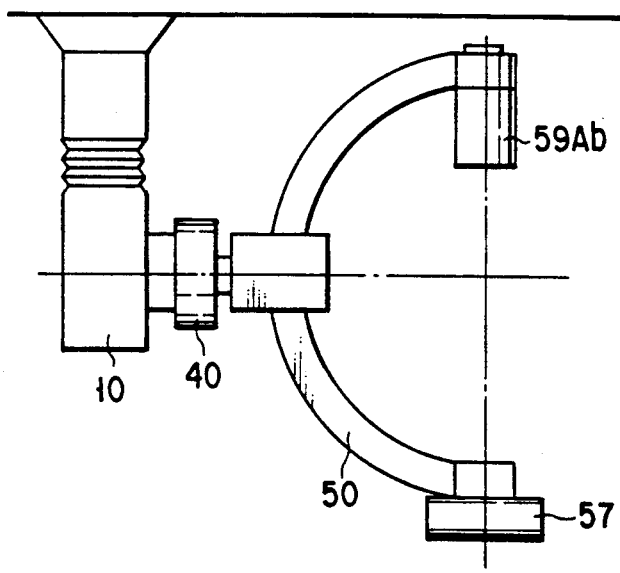
Figure 14C:
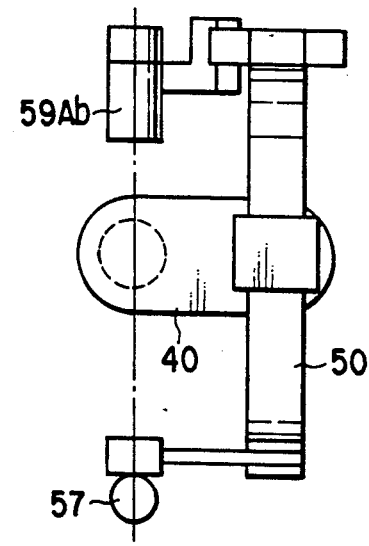
Figure 16A:
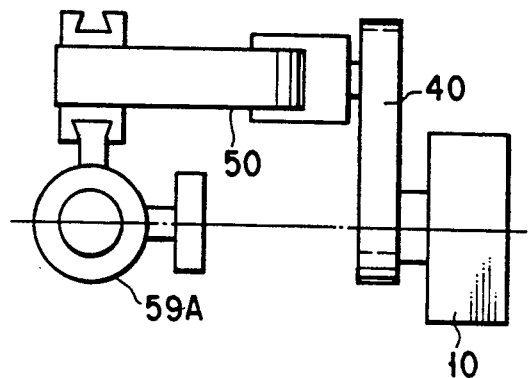
Figure 16B:
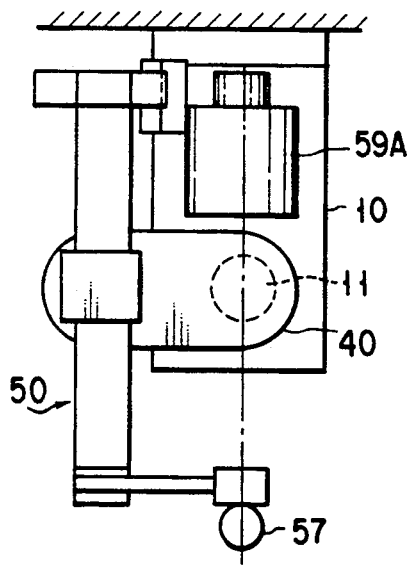
Figure 16C:
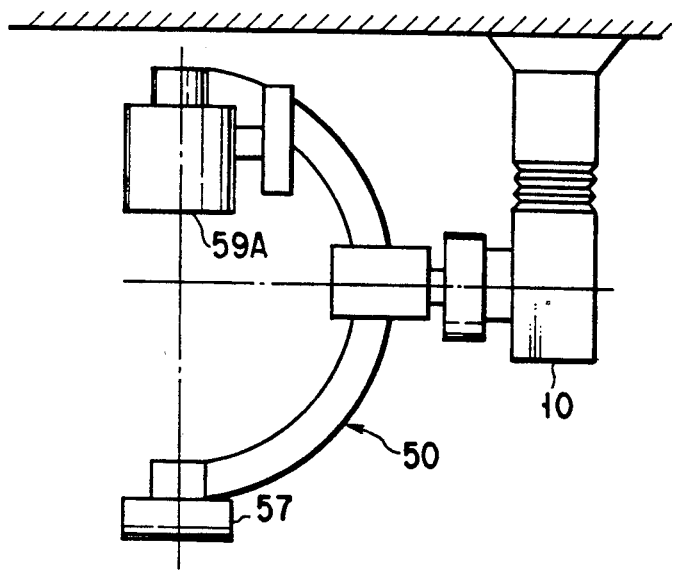

An operation of the above-described apparatus according to the embodiment will now be described. As is shown in FIGS. 14A, 14B and 14C, the apparatus shown in FIG. 3 can be provided with the small-diameter I.I. 59Ab shown in FIGS. 8A, 8B and 8C. In this case, the small-diameter I.I. 59Ab can be brought close to a local part of the subject. Thus, the apparatus with the small-diameter I.I. is suitable for diagnosis of the heart.

Regarding the apparatus shown in FIG. 3 with the X-ray detection unit omitted, the intermediate frame 40 can be rotated about the shaft 11, as shown in FIGS. 15A, 15B and 15C, and the arm apparatus 50 can be rotated about the shaft 51, as shown in FIG. 15D. In addition, the support rod 56B can be rotated about the support pin 56C, as shown in FIG. 15D, in the direction of M5. Thereby, the left-offset arrangement shown in FIG. 3 can easily be changed to the right-offset arrangement. The state of FIG. 15E is shown in greater detain in FIGS. 16A, 16B and 16C.

Figure 17A:
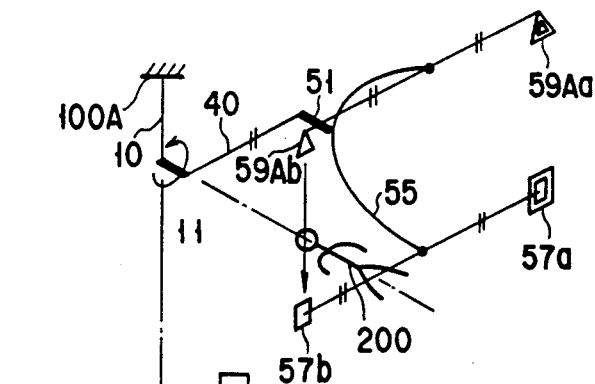
Figure 17B:
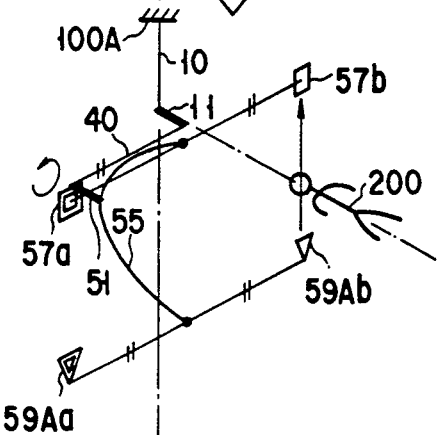
Figure 17C:
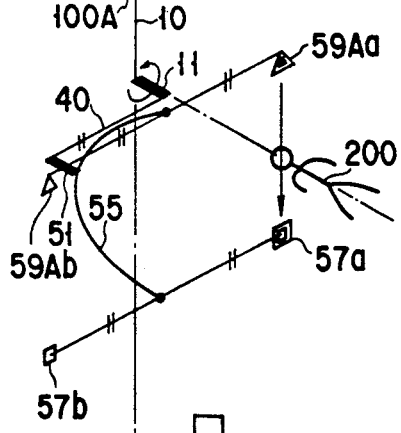
Figure 17D:
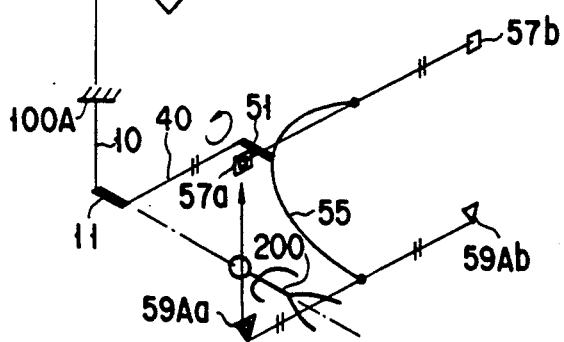

Another operation of the apparatus of this embodiment and the other embodiment will now be described with reference to FIGS. 17A to 17D. The c-arm apparatus 50 shown in FIGS. 17A to 17D has the following structure: the c-arm 55 is provided with the large-diameter I.I. 59Aa and small-diameter I.I. 59Ab, the X-ray generating unit 59a is attached to the large-diameter I.I. 59Aa, and the X-ray generating unit 59b is attached to the small-diameter I.I. 59Ab. FIG. 17A shows the initial state. In the initial state, the under-tube type imaging with the left-offset arrangement can be carried out by using the small-diameter I.I. 59Ab. Subsequently, the shaft 11 is rotated 180° clockwise. Thus, as shown in FIG. 17B, the over-tube type imaging with the right-offset arrangement can be carried out with use of the small-diameter I.I. Then, the shaft 51 is rotated 180° counterclockwise. Thus, as shown in FIG. 17C, the under-tube type imaging with the right-offset arrangement can be carried out with use of the large-diameter I.I. Subsequently, the shaft 11 is rotated 180° counterclockwise, whereby, as shown in FIG. 17D, the over-tube type imaging with the left-offset arrangement can be performed with use of the large-diameter I.I. In FIGS. 17A to 17D, the subject 200 is placed in the fixed position. In the states shown in FIGS. 17A to 17D, if the c-arm 55 is inclined several tens of degrees, a single organ can be fluoroscopically diagnosed or photographed from the right or left.

As has been described above, according to the above embodiment of the invention, the arm apparatus 5, 50 can be provided with more than one pair of desired X-ray generating units 5E, 57 or X-ray detection units 5F, 59. The one or more pairs of X-ray generating units 5E, 57 or X-ray detection units 5F, 59 are freely situated in respect of the subject, with the left-offset arrangement or the right-offset arrangement. Thus, demands for various diagnoses can be met.

Additional advantages and modifications will readily occur to those skilled in the art. Therefore, the invention in its broader aspects is not limited to the specific details, and representative devices, shown and described herein. Accordingly, various modifications may be without departing from the spirit or scope of the general inventive concept as defined by the appended claims and their equivalents.

What is claimed is:

1. An X-ray imaging apparatus for placing in an examination room and for using with a bed which supports a subject comprising:
   a base installed in said examination room;
   an intermediate frame having a horizontal first rotary shaft which is situated along an axis of the subject and a horizontal second rotary shaft, coupled to the base via said horizontal first rotary shaft; and
   an arm apparatus coupled to the intermediate frame via said horizontal second rotary shaft, and having X-ray generating means and X-ray detection means.

2. The apparatus according to claim 1, wherein an imaginary axis of the first rotary shaft differs form an imaginary axis of the second rotary shaft.

3. The apparatus according to claim 1, wherein said base is mounted on one of the ceiling and the floor of the examination room.

4. The apparatus according to claim 1, wherein said base is vertically extendible.

5. The apparatus according to claim 1, wherein an imaginary axis of the first rotary shaft intersects a line connecting the X-ray generating means and the X-ray detection means.

6. An X-ray imaging apparatus for placing in an examination room and for using with a bed which supports a subject comprising:
   a base installed in said examination room;
   an intermediate frame having a horizontal first rotary shaft which is situated along an axis of the subject and a horizontal second rotary shaft, coupled to the base via said horizontal first rotary shaft;
   an arm coupled to the intermediate frame via said horizontal second rotary shaft;
   a first mechanism, provided at one end portion of the arm, for removably supporting at least one X-ray generating means;
   the X-ray generating means supported by the first mechanism;
   a second mechanism, provided at the other end portion of the arm, for supporting at least one X-ray detection means; and
   the X-ray detection means supported by the second mechanism.

7. The apparatus according to claim 6, wherein an imaginary axis of the first rotary shaft differs from an imaginary axis of the second rotary shaft.

8. The apparatus according to claim 6, wherein said base is mounted on one of the ceiling and the floor of the examination room.

9. The apparatus according to claim 6, wherein said base is vertically extendible.

10. The apparatus according to claim 6, wherein an imaginary axis of the first rotary shaft intersects a line connecting the X-ray generating means and the X-ray detection means.

11. An X-ray imaging apparatus for placing in an examination room and for using with a bed which supports a subject comprising:
- a base installed in said examination room;
- an intermediate frame having a horizontal first rotary shaft which is situated along an axis of the subject and a horizontal second rotary shaft, coupled to the base via said horizontal first rotary shaft;
- an arm coupled to the intermediate frame via said horizontal second rotary shaft;
- a first member, provided at one end portion of the arm, for setting at least one X-ray generating means in a predetermined position in a direction perpendicular to the direction in which the arm extends;
- the X-ray generating means supported by the first member;
- a second member, provided at the other end portion of the arm, for setting at least one X-ray detection means in a predetermined position in a direction perpendicular to he direction in which the arm extends; and
- the X-ray detection means supported by the second member.

12. The apparatus according to claim 11, wherein an imaginary axis of the first rotary shaft differs from an imaginary axis of the second rotary shaft.

13. The apparatus according to claim 11, wherein the distance between the position of the X-ray generating means and the arm is substantially equal to the distance between an imaginary axis of the first rotary shaft and an imaginary axis of the second rotary shaft.

14. The apparatus according to claim 11, wherein the distance between the position of the X-ray detection means and the arm is substantially equal to the distance between an imaginary axis of the first rotary shaft and an imaginary axis of the second rotary shaft.

15. The apparatus according to claim 11, wherein the distance between the position of the X-ray generating means and the arm is substantially equal to the distance between the position of the X-ray detection means and the arm and to the distance between an imaginary axis of the first rotary shaft and an imaginary axis of the second rotary shaft.

16. The apparatus according to claim 11, wherein said first member includes a mechanism for connecting/disconnecting the X-ray generating means.

17. The apparatus according to claim 11, wherein said first member includes a mechanism for connecting/disconnecting the X-ray detection means.

18. The apparatus according to claim 11, wherein said first member includes a mechanism for connecting/disconnecting the X-ray generating means, and said second member includes a mechanism for connecting/disconnecting the X-ray detection means.

19. The apparatus according to claim 11, wherein said base is mounted on one of the ceiling and the floor of the examination room.

20. The apparatus according to claim 13, wherein said base is vertically extendible.

21. The apparatus according to claim 11, wherein an imaginary axis of the first rotary shaft intersects a line connecting the X-ray generating means and the X-ray detection means.

* * * * *